United States Patent [19]

Vannus et al.

[11] Patent Number: 5,116,329
[45] Date of Patent: May 26, 1992

[54] MEDICAL LASER INTERCONNECT SYSTEM

[75] Inventors: Tom H. Vannus, Anaheim; Stephen G. Mauser, Tarzana; Wendell V. Ebling, El Toro; Wayne E. Manska, Anaheim, all of Calif.

[73] Assignee: Pfizer Hospital Products Groups, Inc., New York, N.Y.

[21] Appl. No.: 568,549

[22] Filed: Aug. 16, 1990

Related U.S. Application Data

[63] Continuation of Ser. No. 260,242, Oct. 20, 1988, abandoned.

[51] Int. Cl.⁵ .............................................. A61B 17/36
[52] U.S. Cl. ........................................ 606/11; 606/13; 128/6
[58] Field of Search .................................. 606/10–16; 128/395–398, 6

[56] References Cited

U.S. PATENT DOCUMENTS

| | | | |
|---|---|---|---|
| 3,619,037 | 11/1971 | Pugh | 350/269 |
| 3,807,659 | 4/1974 | Winfrey | 244/3.16 |
| 3,931,593 | 1/1976 | Marshall | 331/94.5 |
| 4,103,261 | 7/1978 | Carr | 332/7.51 |
| 4,266,549 | 5/1981 | Kimura | 128/303.1 |
| 4,305,665 | 12/1981 | Achter et al. | 356/339 |
| 4,363,551 | 12/1982 | Achter et al. | 356/338 |
| 4,378,492 | 3/1983 | Nagashima et al. | 250/215 |
| 4,407,272 | 10/1983 | Yamaguchi | 128/6 |
| 4,415,231 | 11/1983 | Kaczensky et al. | 350/269 |
| 4,433,675 | 2/1984 | Konoshima | 128/6 |
| 4,461,005 | 7/1984 | Ward et al. | 372/10 |
| 4,462,661 | 7/1984 | Witt | 350/331 R |
| 4,470,414 | 9/1984 | Imagawa et al. | 128/303.1 |
| 4,474,421 | 10/1984 | Nicholson | 350/3.6 |
| 4,514,079 | 4/1985 | Okada et al. | 355/8 |
| 4,517,974 | 5/1985 | Tanner | 128/303.1 |
| 4,519,390 | 5/1985 | Horne | 128/303.1 |
| 4,524,271 | 6/1985 | Parker | 250/233 |
| 4,526,170 | 7/1985 | Tanner | 128/303.1 |
| 4,537,193 | 9/1985 | Tanner | 128/303.1 |
| 4,549,787 | 10/1985 | Tanner | 350/315 |
| 4,573,467 | 3/1986 | Rich et al. | 128/303.1 |
| 4,580,557 | 4/1986 | Hertzmann | 128/303.1 |
| 4,614,050 | 9/1986 | Stevens | 42/1.01 |
| 4,633,872 | 1/1987 | Chaffee et al. | 128/303.1 |
| 4,635,632 | 1/1987 | Welber et al. | 128/303.1 |
| 4,663,520 | 5/1987 | Tanaka et al. | 250/205 |
| 4,667,922 | 5/1987 | Cutburth et al. | 248/664 |
| 4,669,465 | 6/1987 | Moore et al. | 128/303.1 |
| 4,673,795 | 6/1987 | Ortiz, Jr. | 219/121 L |
| 4,708,126 | 11/1987 | Toda et al. | 128/6 |

FOREIGN PATENT DOCUMENTS 56-15190 1/1981 Japan.
56-59212 5/1981 Japan.
56-10720 8/1981 Japan.

*Primary Examiner*—Max Hindenburg
*Attorney, Agent, or Firm*—Knobbe, Martens, Olson & Bear

[57] ABSTRACT

The present invention comprises a first interconnect assembly and a second interconnect assembly which detachably connects to the first interconnect assembly. One of the interconnect assemblies includes a shutter for blocking an optical path. The first and second assemblies have surfaces which mechanically co-act to drive the shutter away from the optical path. An optical fiber is connected to one of these assemblies. In the preferred embodiment, the first assembly forms a plug and the second assembly forms an adapter, such as a socket. The socket assembly includes a shutter which is spring-biased to a normally closed position. In this normally closed position, the shutter blocks passage of laser light of the optical fiber. The plug assembly includes an appendage having a camming surface which co-acts with a camming surface on the socket assembly so as to drive the shutter to an open position which permits transmission of laser light to the optical fiber.

32 Claims, 3 Drawing Sheets

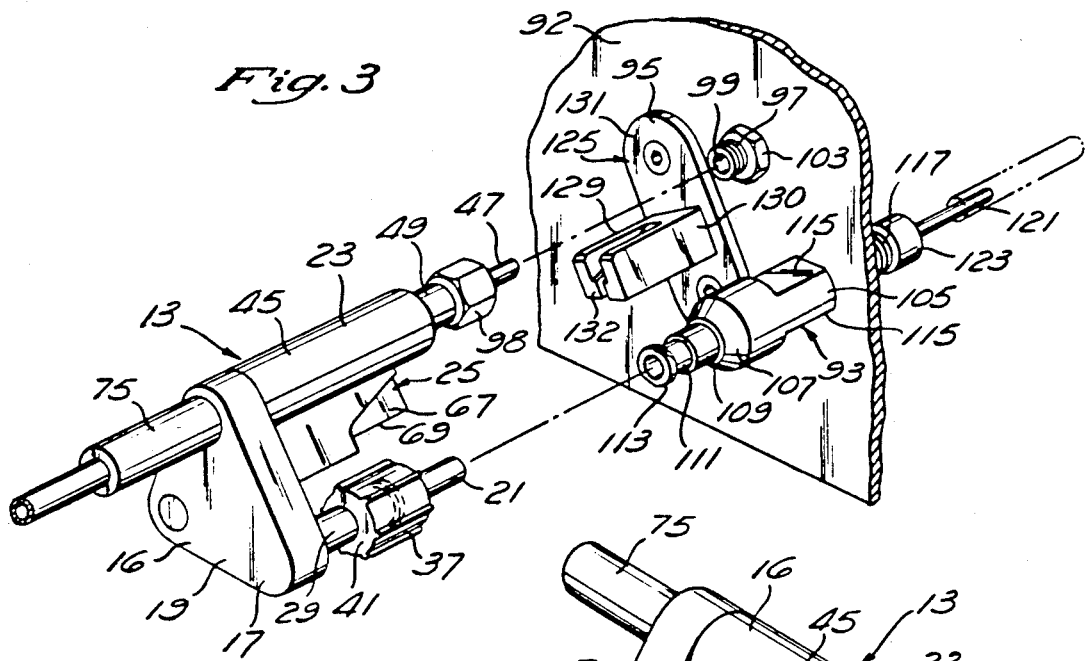
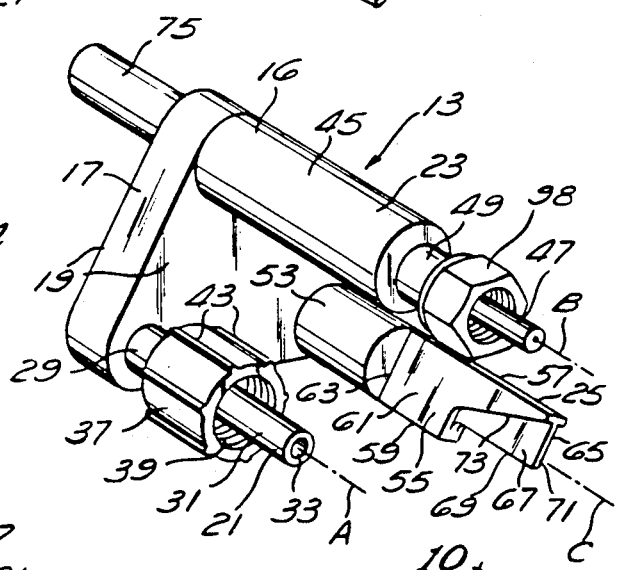
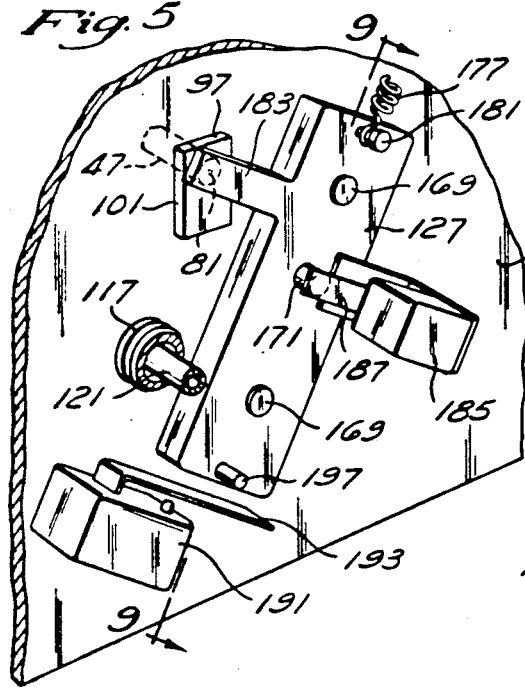

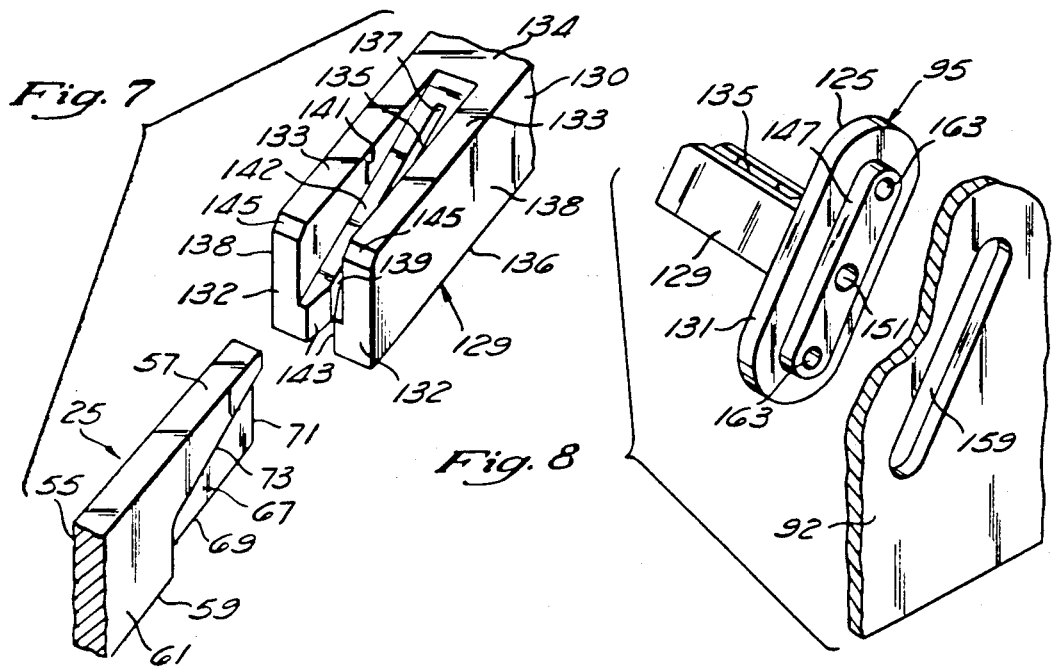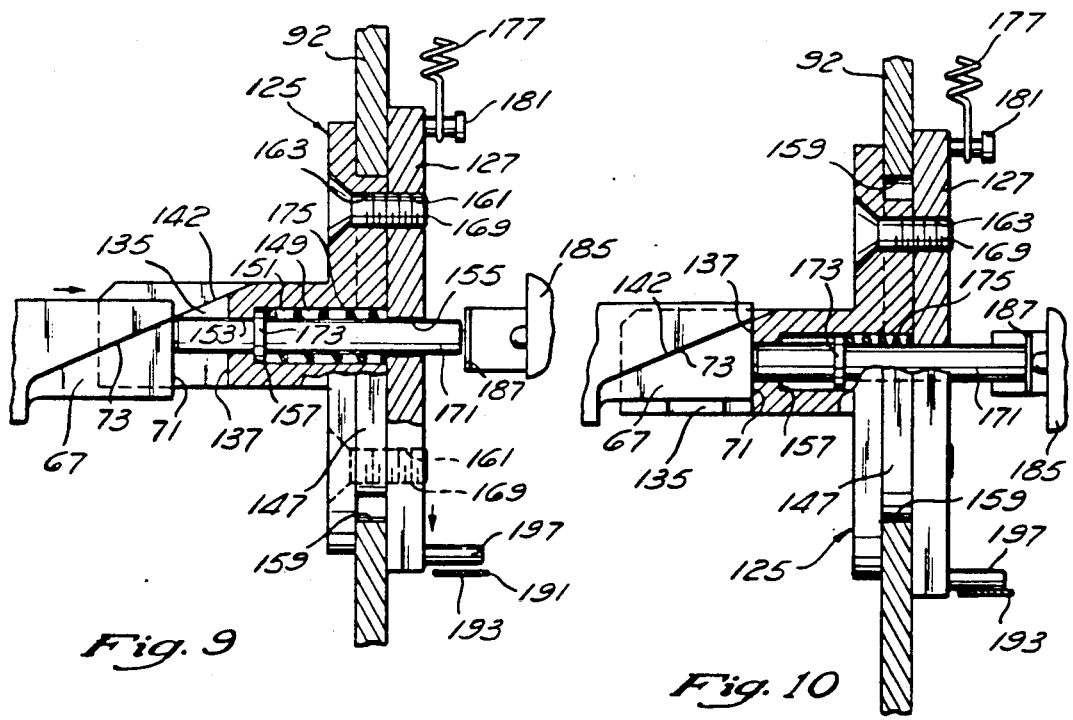

MEDICAL LASER INTERCONNECT SYSTEM

This application is a continuation of application Ser. No. 260,242, filed Oct. 20, 1988, now abandoned.

BACKGROUND OF THE INVENTION

The present invention relates generally to medical laser devices, and particularly to a system for connecting a fiber optic laser catheter to a laser light source or laser beam generator.

Lasers have become increasingly important in medical applications, particularly laser surgery. Typically, light from a laser is delivered to the treatment site by an optical fiber. The wavelength of the laser light is selected for the particular medical application, such as vaporization of tissue or coagulation.

In the prior art, plug-type adapters have been used for connecting the fiber optic laser catheter to the housing of the laser source. A blocking shutter is sometimes used to prevent transmission of light from the laser housing, except when the plug adapter is properly positioned therein. Examples of prior art interconnect systems are disclosed in U.S. Pat. No. 4,633,872, issued to Chaffe, et al. and U.S. Pat. No. 4,415,231, issued to Kaczensky, et al.

SUMMARY OF THE INVENTION

The present invention comprises a first interconnect assembly and a second interconnect assembly which detachably connects to the first interconnect assembly. One of the interconnect assemblies includes a shutter for blocking an optical path. The first and second assemblies have surfaces which mechanically co-act to drive the shutter away from the optical path. An optical fiber is connected to one of these assemblies.

In the preferred embodiment, the first assembly forms a plug and the second assembly forms an adapter, such as a socket. The socket assembly includes a shutter which is spring-biased to a normally closed position. In this normally closed position, the shutter blocks passage of laser light to the optical fiber. The plug assembly includes an appendage having a camming surface which coacts with a camming surface on the socket assembly so as to drive the shutter to an open position which permits transmission of laser light to the optical fiber. Mechanically-actuated sensors on the socket assembly are included to prevent the laser from firing until the plug assembly is fully inserted and properly positioned in the socket assembly. One of these sensors is responsive to a plunger which is actuated by the appendage on the plug assembly. The other is actuated by movement of the shutter.

BRIEF DESCRIPTION OF THE DRAWINGS

These and other features of the invention will now be described with reference to drawings of the preferred embodiment, which is intended to illustrate, and not to limit, the invention, and in which:

FIG. 3 is an enlarged partial exploded perspective view illustrating the mating elements of the plug assembly and socket assembly of the system of FIG. 1;

FIG. 4 is an enlarged perspective view of the plug assembly of FIG. 1;

FIG. 5 is an enlarged rear perspective view illustrating the relaxed state of the mount of the system of FIG. 1;

FIG. 6 is an enlarged rear perspective view illustrating the active state of the mount and sensors of the system of FIG. 1;

FIG. 7 is an enlarged partial perspective view illustrating the mating components of the interlock appendage and the mount of the system of FIG. 1;

FIG. 8 is an enlarged partial perspective view illustrating the mating portions of the mount and body of the socket interconnect assembly of FIG. 1;

FIG. 9 is a partial sectional view illustrating the relaxed state of the mount and sensors of FIG. 1; and FIG. 10 is a partial sectional view illustrating the active state of the mount and sensors of FIG. 1.

DESCRIPTION OF THE PREFERRED EMBODIMENT

Figure 1:
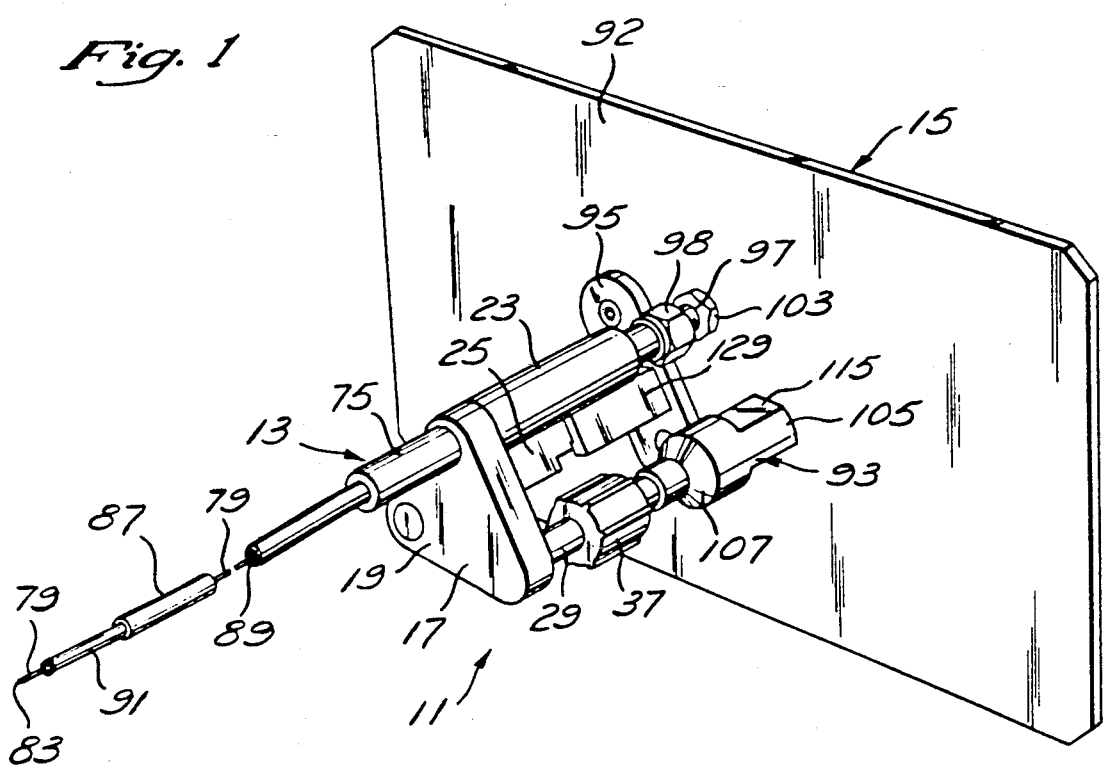
FIG. 1 is a front perspective view of a laser catheter adapter system of the present invention.
Figure 2:
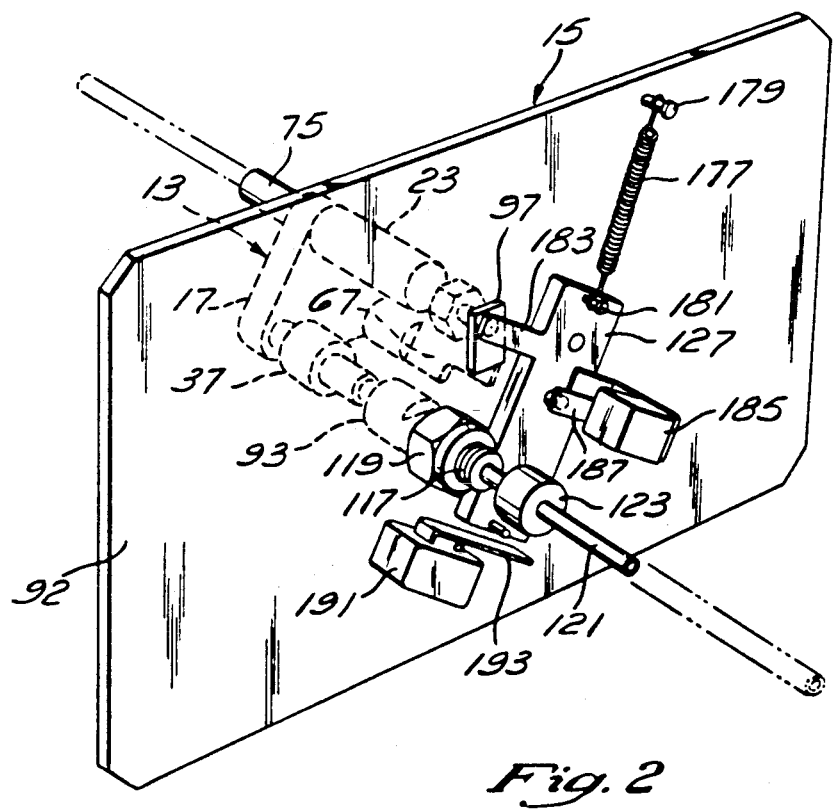
FIG. 2 is a rear perspective view of the socket interconnect assembly of the laser adapter system of FIG. 1, with the plug interconnect assembly shown in phantom.

Referring to FIGS. 1-2, there is shown a laser catheter system 11 including a laser catheter plug interconnect assembly 13 and a socket interconnect assembly 15 for connecting the plug assembly 13 to a radiation beam generator (not shown), such as a high power, medical laser, well known in the art. This system 11 provides a means of preventing the emission of a radiation beam through an interface, unless the catheter plug assembly 13 is properly aligned with the socket assembly 15.

As shown in FIG. 4, the plug assembly 13 includes a housing 16 having a generally triangular base 17 with rounded corners which defines a pair of primary vertical faces 19, and three arms which extend horizontally outward from the corners of one of the vertical faces 19. Specifically, (from the lower left in clockwise order) the arms comprise a generally cylindrical fluid inlet port 21, a generally cylindrical optical fiber housing extension 23, and an interlock appendage 25.

Referring to FIGS. 1, 3 and 4, the catheter plug assembly 13 will now be described in detail. The fluid inlet port 21 may be formed by an elongate cylindrical tube having a larger diameter segment 29 proximate the base 17 of the housing and a smaller diameter segment 31 distal the base 17. The inlet port 21 defines a cylindrical fluid passage 33 which communicates with a fluid passage (not shown) defined by the base 17. A sealing nut 37 surrounds the inlet port 21 and is secured thereto by a raised annular ridge surrounding the smaller diameter segment 31 of the inlet port 21. The sealing nut 37 is generally cylindrical in shape with an internal threaded bore 39. The nut 37 is provided with an overhanging annular flange 41 at one end which is slightly larger than the smaller diameter segment 31 of the inlet port 21 and a series of axially extending ribs 43 to facilitate the gripping of the nut during use.

The fiber housing extension 23 is formed by a primary elongate cylindrical shaft 45 proximate the housing base 17 and a smaller diameter, cylindrical optic fiber guide 47 at the distal end of the shaft 45. A short, medium diameter, transition stage 49 is provided at the distal end of the shaft 45, between the shaft and the guide 47. A female fastener, such as an internally threaded nut, surrounds the transition stage 49, proximate the guide 47, where it is secured by a raised annular surface (not shown).

Referring to FIGS. 4 and 7, the interlock appendage 25 is formed by a cylindrical spacer 53 proximate the base 17 and a narrow, elongate generally rectangular key 55, the height of which is equal to the diameter of the spacer 53. The key 55 has an elongate upper surface 57 and a shorter, elongate lower surface 59, both of which are curved so as to be coplanar with the circumference of the spacer 53. The sides of the key are defined by a pair of planar guide faces 61. The proximal end of the key 55 is integrally joined to the spacer 53 forming a straight inner edge 63. The key 55 has a flat distal surface 65 of T-shaped cross-section and includes a thin blade-shaped tooth 67 formed by a pair of generally triangular cutouts joined along their lower edges. The cutouts begin spaced slightly downward from the upper surface 57 of the key 55 and extend downward and toward the spacer 53 at an approximately 20 degree angle to the upper surface 57 of the key 55. At a point approximately midway between the distal surface 65 of the key and the outer surface of the spacer 53 the cutouts curve sharply, extending vertically downward to the lower surface 59 of the key 55 The tooth 67 is generally triangular with a straight lower surface 69 parallel to, and spaced slightly upward from, the lower edge of the key 55. The tooth 67 has a distal end 71 formed by, and integral with, the stem of the T-shaped distal surface 65 of the key 55. The upper end of the tooth 67 is integrally joined to the key 55, thereby forming a pair of narrow horizontal shoulders 73 extending the length of the cutout between the guide faces 61 and the upper end of the tooth 67. Desirably, the tooth 67 is significantly narrower than the diameter of a standard paper clip (approximately 0.038 inches), the significance of which will be described below.

The arms extend perpendicularly outward from the base 17 of the housing 16, forming an equilateral triangle. The inlet port 21 defines a fluid passage 33 having an axis A. The fiber housing extension 23 defines an axis B spaced from and parallel to the axis A of the fluid passage 33. The spacer 53 of the interlock appendage 25 defines an axis C which is spaced from and parallel to both the axis A of the fluid passage 33 and the axis C of the fiber housing extension 23.

As shown in FIGS. 1 and 2, a cylindrical outlet port 75 extends horizontally outward from the base 17 of the housing immediately opposite the fiber housing extension 23. The outlet port 75 defines a cylindrical fluid passage (not shown) which is coaxial with the axis of the fiber housing extension 23. An elongate optical fiber 79 extends coaxially from the optic fiber guide 47, through the fiber housing extension 23 and significantly beyond the outlet port 75. The optical fiber 79 has a receiving end 81 secured within the distal end of the optical fiber guide 47 and a delivery end 83 opposite the receiving end 81. When a radiation beam emitted by a beam generator is properly aligned with the receiving end 81 of the fiber, the beam is conducted through the fiber to the delivery end 83 of the fiber where it is focused by a lens (not shown) onto the operative site.

A sheath 87 extends from the outlet port 75 to proximate the delivery end 83 of the fiber. The sheath 87 is coaxial with the optical fiber 79 and has an internal diameter significantly greater than the external diameter of the optical fiber 79, thereby forming an annular fluid path 89 about the optical fiber 79. The fluid is used both as a coolant and as a means to minimize back-splatter during operation. The delivery end 83 of the fiber is secured proximate the lens by a rigid tip 91. The tip 91 maintains the fiber 79 in proper alignment with the lens and stiffens the operative end of the plug assembly 13 to enable it to be inserted into a vein or other body opening.

Referring now to FIGS. 1 and 3, the socket assembly 15 will be described in greater detail. As discussed above, the socket assembly 15 includes a body 92 provided with three receptacles for mating and retaining the arms of the plug assembly 13. Specifically, the socket assembly 15 is provided with (from the lower right in clockwise order) a fluid-tight fitting 93 which mates with the inlet port 21, a movable mount 95 which mates with the interlock appendage 25 and an externally threaded male fastener 97 which mates with the fiber housing extension 23 and which defines an optical port 99 which forms the interface between the beam generator and the plug assembly 13. The male fastener 97 extends through and is secured within a mating aperture in the body 92 of the socket assembly 15.

As shown in FIG. 5, the male fastener 97 includes a flat rectangular head 101 larger in diameter than the mating aperture in the body 92 of the socket assembly 15. The male fastener 97 is desirably secured within the aperture by an internally threaded hex nut 103 which leaves a sufficient portion of the threads of the male fastener 97 exposed to permit the external threads of the male fastener 97 to receive and retain the internal threads of the female fastener 98 which surrounds the fiber housing extension 23. The male fastener 97 defines an interface or throughbore which permits a beam generated by the beam generator to be transmitted by the optical fiber 79 from its receiving end 81 to its delivery end 83.

Referring to FIGS. 2 and 3, the fitting 93 extends through and is secured within a mating aperture in the body 92. The fitting 93 is a standard fluid tight SMA connector including a generally cylindrical trunk 105, a beveled end 107 and a cylindrical cup-shaped, spring loaded core 109. A cylindrical extender 111, including an outwardly extending sealing ring 113, fits tightly within the core. The trunk is provided with a pair of elongate detents 115 to facilitate the tightening of the fitting 93 to the body 92. The section of the fitting 93 extending through the aperture behind the body 92 is provided with a set of external threads 117 which mate with an internally threaded lock nut 119 to secure the fitting 93 to the body 92 of the socket assembly 15. A cylindrical connecting tube 121 extends through the fitting's set of external threads and is press fit within a mating bore in the spring-loaded core 109. The connecting tube 121 permits fluid communication between a pressurized fluid source (not shown) and the core. A cylindrical stop 123 is secured to the connecting tube 121 so as to limit the movement of the core relative to the cylindrical trunk.

Referring to FIGS. 1, 2, 3 and 7, the mount 95 is formed by a slide 125 which mates with the interlock appendage 25 and a backing plate 127, opposite the body 92 from the slide 125. The slide 125 is formed by an elongate generally rectangular fork 129 and a planar oblong panel 131. The fork 129 has a proximal end 130, a distal end 132, a top surface 134, a bottom surface 136 and a pair of generally rectangular sides 138. The proximal end 130 of the fork 129 is fixed to the middle of the oblong panel 131. The fork 129 is divided into a pair of prongs 133 by a narrow vertical channel 135, centered between the sides 138 of the fork 129 having a closed end 137 and an open mouth 139. Extending downward toward the distal end 132 of the fork 129 at an angle of approximately 20 degrees from the top surface 134 of the fork 129 is a generally triangular cutout approximately five times wider than the width of the channel 135. The cutout extends from the upper surface 134 of the fork 129, spaced slightly toward the proximal end 130 of the fork 129 from the closed end 137 of the channel 135, to the distal end 132 of the fork 129, spaced slightly above the bottom surface 136 of the fork 129. The cutout forms a pair of vertical triangular inner faces 141 and a pair of horizontal ledges 142 extending between the upper edges of the channel 135 and the lower edges of the inner faces 141 Beyond the mouth 139 of the channel 135, the prongs are beveled outward forming a pair of vertical guide surfaces 143. In addition, a pair of slightly downwardly bevelled corners 145 is provided at the upper edge of the distal end of the fork 129.

As shown in FIG. 8, the panel 131 is provided with a raised oblong alignment member 147 in the middle of the panel 131 opposite the fork 129. As shown in FIGS. 9 and 10, a bore 149 extends from the alignment member 147 to the closed end 137 of the channel 135. The bore 149 includes a larger diameter section 151 extending substantially the length of the bore from the alignment member 147 and a smaller diameter section 153 proximate the closed end 137 of the channel 135. The backing plate 127 is provided with a plunger bore 155 corresponding in size and position to the larger diameter section 151 of the bore 149 of the slide 125. An annular stop 157 is formed by the junction of the two sections of the bore 149.

As discussed in greater detail below, the alignment member 147 cooperates with a mating, slightly longer and wider slot 159 in the socket assembly 15 body 92. The slot 159 extends parallel to the axes of the optic port and the inlet port. Referring to FIG. 9, the backing plate 127 and the slide 125 are provided with a pair of corresponding bores 161, 163 which extend through the ends of the backing plate 127 and the alignment member 147, respectively. A pair of bolts 169, or other suitable fasteners, secure the alignment member 147 of the slide 125 in slidable engagement with the body 92. Desirably, the bores of the slide 125 are countersunk.

A generally cylindrical plunger 171 having a diameter slightly smaller than the diameter of the smaller section of the bore 149 is secured within the bore 149 by an annular collar 173 having a diameter slightly smaller than the diameter of the larger diameter section 151 of the bore 149. The collar 173 of the plunger 171 is biased into engagement with the annular stop 157 of the bore 149 by a helical spring 175 which is compressed between the backing plate 127 and the collar 173. In this position, one end of the plunger 171 extends through the smaller diameter section 153 of the bore 149 roughly one eighth inch into the fork 129 channel 135 and the opposite end of the plunger 171 extends through the larger diameter section 151 of the bore 149 roughly one eighth inch beyond the backing plate 127. As shown in FIGS. 2, 5 and 9, in its relaxed state (before the distal end 71 of the tooth 67 overcomes the bias of the spring and moves the plunger 171), a biasing element 177, such as a tensioned helical spring having one end secured to an anchor 179 near the upper end of the body 92 and another end secured to a hook 181 near the top end of the backing plate 127, biases the alignment member 147 into engagement with the top of the slot 159. A generally rectangular shutter 183 extending perpendicularly from the backing plate 127 is provided which covers the interface when the system 11 is in its relaxed state, thereby preventing a laser beam from passing through the interface and causing damage.

Referring to FIGS. 9 and 10, as the distal end 71 of the tooth 67 is inserted further into the channel 135, the horizontal shoulders 73 of the appendage 25 cooperate with the horizontal ledges 142 of mount 95 to overcome the bias of the biasing element 177, resulting in the downward movement of the mount 95. As shown in FIG. 10, in its active state (i.e., when the distal end 71 of the tooth 67 is in engagement with the closed end 137 of the channel 135), the alignment member 147 is flush against the lower end of the slot 159, one end of the plunger 171 is flush with the closed end of the channel 135 and the opposite end of the plunger 171 extends through the larger diameter section 151 of the bore 149 approximately one quarter inch beyond the backing plate 127. As illustrated in FIG. 6, in its active state, the shutter 183 exposes the interface, thereby permitting a laser beam to pass therethrough and into the optical fiber.

As a further feature to minimize the risk that a laser beam will be emitted through the interface before the plug assembly 13 is fully engaged, the socket assembly 15 is provided with a first microswitch 185, of a nature well known in the art, which senses that the distal end 71 of the tooth 67 has moved far enough toward the end of the channel 135 to ensure that the optical fiber 79 is properly aligned with the radiation beam. The microswitch 185 is desirably provided with a normally open contact 187 and is secured to the backing plate 127 proximate the mouth 139 of the plunger 171 bore 149. The microswitch 185 operates a control line to a microprocessor (not shown) which disables the beam generator until the force of the plunger 171 closes the contact.

As yet another means of avoiding the emission of a laser beam through the interface before the plug assembly 13 is fully engaged, the socket assembly 15 is provided with a second microswitch 191, similar to the first microswitch 185, which operates a control line to a microprocessor which disables the beam generator until the microswitch 191 senses the sufficient downward movement of the mount 95 to ensure that the optical fiber 79 is in alignment with the beam generator. The microswitch 191 is desirably provided with a normally open contact 193 and is secured to the body 92 proximate the lower end of the range of movement of the backing plate 127. The second microswitch 191 is desirably actuated by the movement of a pin 197 fixed to and extending horizontally outward from the backing plate 127. Upon sufficient insertion of the tooth 67 into the channel 135 to ensure that the optical fiber 79 is properly aligned with the radiation beam, movement of the mount 95 forces the pin 197 against the normally open contact 193 closing the contact, thereby permitting the activation of the beam generator.

OPERATION

The operation of the laser catheter adapter will now be briefly described.

As shown in FIGS. 2, 5 and 9, in its relaxed state, the mount 95 of the socket assembly 15 is biased against the upper end of the slot 159 of the assembly body 92 so that the assembly interface is covered by the shutter 183. As best seen in FIG. 9, one end of the plunger 171 extends beyond the closed end 137 of the channel 135 and the opposite end extends approximately ⅛-inch from the backing plate 127 but is slightly spaced from the normally open contact of the first microswitch 185. Likewise, the pin 197 extending from the lower end of the backing plate 127 is proximate to, but spaced from, the normally open contact 193 of the second microswitch 191.

The plug interconnect assembly is then inserted into the socket interconnect assembly by means of aligning the optical fiber guide 47 with the optical port 99 of the male fastener 97, the smaller diameter segment 31 of the inlet port 21 with the bore of the adapter's extender 111 and the key 55 of the interlock appendage 25 with the cutout of the mount 95. Although the fiber housing extension 23 is longer than the interlock appendage 25 or the inlet port 21, the mount 95 is sufficiently longer than the male fastener 97 so that as the optical fiber guide 47 is inserted into the optical port 99 of the male fastener 97, the guide surfaces 143 at the mouth 139 of the channel 135 direct the tooth 67 of the interlock appendage 25 toward the center of the channel 135. As the horizontal shoulders 73 of the interlock appendage 25 cooperate with the horizontal ledges 142 of the mount 95, the smaller diameter segment 31 of the inlet port 21 is inserted within the extender 111 of the fitting 93.

As shown in FIG. 2, the plug assembly 13 can be inserted into the socket assembly 15 without the system 11 permitting the beam generator to generate a laser beam. To permit a laser beam to be generated, the female fastener 97 of the fiber housing extension 23 must be fully tightened against the hex nut surrounding the male fastener 97 of the socket assembly 15, causing the key 55 to move within the channel 135 and the inlet port 21 to be sealably connected to the extender 111 of the fitting 93, thereby assuring (1) that a beam will not be emitted from the system unless the optical fiber 79 is precisely aligned with the beam generator and (2) that a radiation will not be generated until the inlet port 21 is sealably secured to the fitting 93, thereby insuring the proper cooling of the tip 91 of the laser catheter. Desirably, the sealing nut is tightened over the sealing ring of the fitting's extender to further ensure that the integrity of the fluid seal is maintained.

As shown in FIGS. 6 and 10, in its active position, the distal end 71 of the tooth 67 contacts the closed end 137 of the channel 135, forcing the plunger 171 outward from the packing plate approximately ¼-inch, thereby actuating the first microswitch 185, so that the switch no longer disables the beam generator. In addition, the cam action of the horizontal shoulders 73 of the key 55 and the horizontal ledges 142 of the mount 95, drive the mount 95 against the bottom of the slot 159 and the pin 197 extending from the backing plate 127 against the normally open contact of the second microswitch 191 so that the laser is no longer disabled by the second microswitch 191. Finally, the movement of the mount 95 causes the shutter 183 to uncover the interface, permitting a beam to be emitted from the beam generator, through the receiving end 81 of the optical fiber 79, so that it may be transmitted to the delivery end 83 of the optical fiber 79 where it can be focused by a lens upon the operative site.

It is significant that the triangular configuration of the laser catheter adapter system 11 of the present invention provides a connection of superior strength and durability. Furthermore, as the movement of the mount 95 in the slot 159 is parallel to a line connecting the axis of the male fastener 97 and fitting 93, it is difficult to overcome the safety features of the invention by permanently biasing the mount 95 downward, for example, through the use of a rubberband extending about the mount 95, a fiber housing and an inlet port 21.

In addition, as a precaution against operators successfully biasing the mount 95 downward to actuate the second microswitch 191 and open the shutter 183, the mount's channel 135 is significantly narrower than a standard paper clip, thereby preventing the operator from actuating the first microswitch 185 by simply inserting a paper clip into the channel 135.

Accordingly, there is provided a simple, yet reliable, laser catheter adapter system which effectively and conveniently satisfies the needs of the prior art.

We claim:

1. A medical device, comprising:
 a medical laser for producing light for propagation along an optical path;
 a first interconnect assembly; and
 a second interconnect assembly for detachably connecting with said first interconnect assembly, one of said interconnect assemblies including a shutter for blocking said optical path, said first and second assemblies having camming surfaces which mechanically co-act to drive said shutter relative to said optical path;
 optical guide means connected to one of said interconnect assemblies, for receiving light from said optical path; and
 an optical port on another of said interconnect assemblies, for engaging said optical guide means, said engagement of said guide means and said optical port being independent of said mechanical co-action of said camming surfaces.

2. A medical device, as defined by claim 1, wherein one of said interconnect assemblies comprises a switch and a switch activating member, and the other of said interconnect assemblies comprises an appendage, said switch activating member responsive to said appendage to change the state of said switch.

3. A medical device, as defined by claim 2, wherein one of said interconnect assemblies includes a second switch responsive to said driving of said shutter to change the state of said second switch.

4. A medical device, as defined by claim 1, wherein said optical guide means comprises an optical fiber.

5. A medical device, as defined by claim 4, wherein said optical fiber is disposed in a catheter.

6. A medical device, as defined by claim 1, wherein said camming surfaces comprise a first surface on a channel of said first interconnect assembly and a second surface on an appendage of said second interconnect assembly.

7. A medical device, as defined by claim 6, wherein said channel is sized to prevent passage of a standard paper clip therethrough.

8. A medical device, as defined by claim 1, wherein one of said interconnect assemblies comprises a fluid port and the other of said interconnect assemblies comprises a fitting for sealably connecting to said fluid port to provide fluid communication between said interconnect assemblies.

9. A medical device, as defined by claim 1, wherein said first interconnect assembly comprises a socket and wherein said second interconnect assembly comprises a plug.

10. A medical device, as defined by claim 9, wherein the plug interconnect assembly comprises a housing, a fluid inlet, and an appendage, said inlet and said appendage extending outward from said housing parallel to each other, said appendage extending a greater distance from said housing than said fluid inlet.

11. A medical device as defined by claim 9, wherein the plug interconnect assembly comprises an appendage and the socket interconnect assembly comprises a mount, said socket interconnect assembly further comprising a mechanically actuated sensor actuated by movement of said mount in response to insertion of said appendage into a channel formed in said mount, said socket interconnect assembly further comprising a biasing member for resisting the movement of the mount in response to the insertion of the appendage into the channel.

12. A medical device as defined by claim 9, wherein the plug interconnect assembly comprises a housing, an optical guide extension, a fluid inlet, and an appendage, said extension extending further from said housing than said appendage, and said appendage extending further from said housing than said fluid inlet.

13. A medical device, as defined by claim 12, wherein said appendage, extension, and fluid inlet are mounted in triangular relationship.

14. A medical device, as defined by claim 13, wherein said extension and said fluid inlet are disposed such that they lie along a line parallel to the direction of movement of said shutter.

15. A medical device, comprising:
a first interconnect assembly;
a second interconnect assembly for detachably connecting with said first interconnect assembly, one of said interconnect assemblies comprising a housing and an appendage extending from said housing, and the other of said interconnect assemblies comprising (i) a body having an optical port through which a radiation beam along an optical path may pass, (ii) a shutter for blocking said optical path, and (iii) a mount for mating with said appendage, said mount and said appendage having respective surfaces which mechanically coact to move said mount in response to the insertion of a portion of said appendage into said mount to drive said shutter away from said optical path, said surface on said mount being inaccessible from inside said optical port to prevent said shutter from being driven through said optical port; and
an optical fiber, connected to one of said interconnect assemblies.

16. The device of claim 15, wherein said co-acting surfaces comprise a cam surface and a cammed surface for imparting movement to said shutter.

17. The device of claim 15, wherein said channel has a mouth small enough to prevent the entry therein of a standard paper clip.

18. The device of claim 17, wherein one of said interconnect assemblies further comprises a biasing member for resisting the movement of said mount in response to the insertion of said portion of said appendage into said channel.

19. The device of claim 15 wherein one of said interconnect assemblies further comprises a mechanically actuated sensor actuated by the movement of said mount in response to the insertion of said portion of said appendage into said mount.

20. The device of claim 19, wherein said sensor comprises a mechanically actuated electrical microswitch.

21. The device of claim 15, wherein said optical port does not move in response to the movement of said mount.

22. The device of claim 15, wherein the movement of said mount is perpendicular to said optical path.

23. The device of claim 15, wherein said shutter is attached to said mount.

24. A medical device, comprising:
a medical laser for producing light for propagation along an optical path; and
an interconnect device comprising a plug interconnect assembly and a socket interconnect assembly, said plug interconnect assembly comprising an appendage having a key portion and a camming surface, said socket interconnect assembly having a channel sized to receive said key portion and a camming surface which co-acts with said camming surface of said plug interconnect assembly, said socket interconnect assembly having an optical port and a shutter for selectively blocking or opening said optical path in response to relative movement of said camming surfaces, said channel being inaccessible from inside said optical port.

25. A medical device, as defined by claim 24, wherein said socket interconnect assembly additionally comprises a plunger responsive to said key portion of said appendage, and a switch mounted on said shutter such that said plunger actuates said switch upon insertion of said key portion into said channel.

26. A medical device, as defined by claim 25, wherein said socket interconnect assembly additionally comprises a second switch positioned for activation upon movement of said shutter.

27. A medical device, comprising:
an interconnect assembly for actuating movement of a shutter to selectively open or block an optical port of a medical laser, said interconnect assembly comprising an interlock appendage having a surface for mechanically actuating said shutter, and an optical guide configured to mate with said optical port to receive transmission of light from said medical laser, said appendage being independent of said optical guide such that said mechanical actuation of said shutters is independent of the mating of the optical guide with the optical port.

28. A medical device, comprising:
an interconnect assembly having an optical guide for connecting to a medical laser, said interconnect assembly comprising an appendage having a thickness of less than approximately 0.038 inches, said appendage being configured to mechanically drive a shutter on the medical laser to control transmission of laser light to said optical guide.

29. A medical device, as defined by claim 28, wherein said optical guide comprises an optical fiber.

30. A medical device, as defined by claim 28, wherein said interconnect assembly comprises a plug and said complementary interconnect assembly comprises a socket.

31. A medical device, as defined by claim 28, wherein said surface is configured as a camming surface.

32. A method of operating a medical laser, comprising:
inserting a plug interconnect assembly into a socket interconnect assembly.
utilizing a camming surface on an interlock appendage of said plug assembly to mechanically drive a shutter on said socket assembly;
sensing when said interlock appendage is in position to drive said shutter;
sensing when the shutter has been driven by the appendage; and
activating said medical laser only after said sensing steps confirm that said appendage is in position and said shutter has been driven by said appendage.

* * * * *